United States Patent [19]
Galey et al.

[11] Patent Number: 5,629,436
[45] Date of Patent: May 13, 1997

[54] USE OF N-ARYLMETHYLENE ETHYLENEDIAMINETRIACETATES N-ARYLMETHYLENE IMINODIACETATES OR N,N'-DIARYLMETHYLENE ETHYLENEDIAMINEACETATES AGAINST OXIDATIVE STRESS

[75] Inventors: Jean-Baptiste Galey, Paris; Jacqueline Dumats, Villepinte, both of France

[73] Assignee: L'Oreal, Paris, France

[21] Appl. No.: 469,751

[22] Filed: Jun. 6, 1995

Related U.S. Application Data

[62] Division of Ser. No. 436,203, filed as PCT/FR93/01109, Nov. 10, 1993.

[30] Foreign Application Priority Data

Nov. 13, 1992 [FR] France ..................... 92 13707
Jun. 23, 1993 [FR] France ..................... 93 07641

[51] Int. Cl.$^6$ .......................... C07F 15/02; C07C 229/24
[52] U.S. Cl. ..................... 556/148; 560/17; 560/38; 560/39; 560/22; 562/426; 562/435; 562/443; 562/449; 562/453
[58] Field of Search ..................... 562/426, 435, 562/443, 449, 453; 560/22, 17, 38, 39; 556/148

[56] References Cited

U.S. PATENT DOCUMENTS 4,528,196  7/1985  Pitt .......................... 514/533

FOREIGN PATENT DOCUMENTS 0367223  9/1990  European Pat. Off. .

OTHER PUBLICATIONS

American Journal of Hematology, vol. 24, No. 3, Mar. 1987, pp. 277–284.

Inorganica Chimica Acta, vol. 138, No. 3, 1987, pp. 215–230.

Chemical Abstracts, vol. 110, No. 3, 27 Mar. 1989, No. 110927.

Pitt, C.G., et al, "Esters and Lactones of Phenolic Amino Carboxylic Acids: Prodrugs for Iron Chelation", J. Med. Chem., vol. 29, No. 7, Jul. 1986, pp. 1231–1237.

*Primary Examiner*—Joseph Conrad
*Attorney, Agent, or Firm*—Jacobson, Price, Holman & Stern, PLLC

[57] ABSTRACT

N-arylmethylene ethylenediaminetriacetate, N-arylmethylene iminodiacetate or N,N'-diarylmethylene ethylenediaminediacetate type compounds and their use in combatting oxidative stress, and pharmaceutical and cosmetic compositions comprising said compounds. The invention also concerns a process for the preparation of said compounds.

2 Claims, No Drawings

USE OF N-ARYLMETHYLENE ETHYLENEDIAMINETRIACETATES N-ARYLMETHYLENE IMINODIACETATES OR N,N'-DIARYLMETHYLENE ETHYLENEDIAMINEACETATES AGAINST OXIDATIVE STRESS

This is a divisional U.S. patent application of Ser. No. 08/436,203, filed as PCT/FR93/01109, Nov. 10, 1993.

The present invention relates to N-arylmethylene ethylenediaminetriacetate, N-arylmethylene iminodiacetate or N,N'-diarylmethylene ethylenediamineacetate derivatives which are useful in particular for protecting the body against oxidative stress, to their process of preparation and to the pharmaceutical and cosmetic compositions containing such compounds.

In the field of health and cosmetics, the concept of oxidative stress is known, which oxidative stress appears in particular as soon as a disequilibrium exists in the antioxidant/prooxidant balance. This imbalance is reflected in particular in uncontrolled oxidative processes within living tissue which involve oxygenated free radicals and which lead in particular to oxidative damage to biological molecules and macromolecules (Sies, H., in Oxidative Stress, Academic Press Inc. (London) Ltd., 1985).

It is known that various situations cause, promote or accompany oxidative stress or are the consequence thereof; they are in particular exposure to ultraviolet or to ionizing radiation, aging, inflammation, carcinogenesis, ischemic reperfusion situations, or the toxicity and/or method of action of certain medicaments.

During this oxidative stress phenomenon, it is known that iron is released from it usual storage sites, such as ferritin, and, when released, can take part in certain reactions, and in particular the Fenton (1) and Haber-Weiss (2) reactions, which result in the formation of hydroxyl radicals, which radicals are known to be responsible for much oxidative damage (Reif, D. W., Free Rad. Biol. Med. 12, 417–427, 1992).

Oxygen is essential for respiration in aerobic living beings but can be reduced to the superoxide radical $O_2^{\circ-}$ in all aerobic cells. This radical can undergo a disproportionation reaction which gives rise to hydrogen peroxide:

$$2O_2^{\circ-} + 2H^+ \rightarrow H_2O_2 + O_2$$

In the presence of traces of iron, this superoxide radical can also reduce the $Fe^{3+}$ ion:

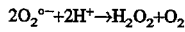

$$O_2^{\circ-} + Fe^{3+} \rightarrow Fe^{2+} + O_2$$

The $Fe^{2+}$ ions thus produced can give rise to the Fenton reaction which produces the hydroxyl radical:

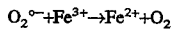

$$H_2O_2 + Fe^{2+} \rightarrow OH^\circ + OH^- + Fe^{3+} \quad (1)$$

The Haber-Weiss reaction also produces hydroxyl radicals:

$$H_2O_2 + O_2^{\circ-} \xrightarrow{Fe^{3+}} OH^\circ + OH^- + O_2 \quad (2)$$

The hydroxyl radical $OH^\circ$ can cause very serious damage in the body. It is capable of breaking DNA strands and or detrimentally affecting the gene pool of the living cell. In contrast to $H_2O_2$ and to the superoxide radical $O_2^{\circ-}$ it is also capable of causing peroxidation of the unsaturated fatty acids. It plays a significant role in skin aging.

It is known that protection of living tissues against attacks by the hydroxyl radical is difficult.

One of the known approaches for self-protection is to use molecules, in particular D-mannitol or DMSO (dimethyl sulfoxide), which are capable of scavenging the hydroxyl radicals. Nevertheless, the hydroxyl radical is such a reactive species that it is necessary to use very large amounts of these scavengers, so as to compete with all the biological molecules which are potential targets for the hydroxyl radical (Halliwell, B., Free Rad. Res. Comms., 9(1), 1–32, 1990). The use of large amounts of these scavengers poses problems of toxicity.

The other known approach for self-protection against hydroxyl radicals is to use chelating agents for iron, in particular deferoxamine or diethylenetriaminepentaacetic acid (DTPA), in order to prevent it from participating in the Fenton and Haber-Weiss reactions.

However, although their complexation constants are high, these chelating agents can be toxic. Thus it is that DTPA has serious side effects, probably partly related to the chelation of metals such as calcium.

Deferoxamine has a presumed chronic toxicity related to its ability to chelate the metals of the active sites of metalloenzymes or hemoproteins, such as hemoglobin.

Moreover, powerful chelating agents, which can complex iron, such as EHPC (ethylenebis-o-hydroxyphenylglycine), are also known to have high acute toxicities.

Finally, HBED-DME, that is to say the dimethyl ester of N,N'-bis(2-hydroxybenzyl)ethylenediaminediacetic acid, is described as an exceptionally efficient chelating agent for iron in U.S. Pat. No. 4,528,196 and in the publication "American Journal of Hematology" Vol 24, No 3, March 1987 HBED, that is to say N,N'-bis(2-hydroxybenzyl) ethylenediaminediacetic acid, is described in Chemical Abstracts, Vol. 110, 1989, 110927e, as a sequestering agent for actinides. These compounds also exhibit risks of toxicity because they form very stable complexes, all the coordination sites of the iron being occupied due to the presence of the OH groups at the 2-position.

The Applicant company has discovered that N-arylmethylene ethylenediaminetriacetate, N-arylmethylene iminodiacetate or N,N'-diarylmethylene ethylenediaminediacetate derivatives are particularly efficient in protecting the body against oxidative stress.

Without being limited to this explanation, it seems that this effect is due to the property of these derivatives not only to form complexes with iron but also virtually stoichiometrically to scavenge hydroxyl radicals before they can attack other molecules.

Indeed, the compounds according to the invention form complexes with the $Fe^{2+}$ ion and these complexes are capable of decomposing hydrogen peroxide without releasing hydroxyl radicals. These radicals are, in fact, formed but immediately scavenged by an intramolecular hydroxylation process, which makes it possible to use only very low concentrations of the molecules according to the invention. This last point constitutes an advantage with respect to the other scavengers of hydroxyl radicals already mentioned which need to be used in very large excess.

Another advantage of the compounds according to the invention is that they form with iron complexes whose association constants are much lower than those of the compounds mentioned above, such as deferoxamine or HBED. The toxicological risks are thus reduced.

Finally, the products of the intramolecular hydroxylation of the ferrous complexes of the molecules according to the invention have a high affinity for iron and form, with the latter, complexes capable of preventing it from catalysing the formation of other hydroxyl radicals.

The subject of the invention is the use, for protecting the body against oxidative stress and in particular as scavengers of free hydroxyl radicals and chelating agents for iron, of N-arylmethylene ethylenediaminetriacetate, N-arylmethylene iminodiacetate or N,N'-diarylmethylene ethylenediaminediacetate derivatives.

Another subject consists of the cosmetic and pharmaceutical compositions implementing them.

Another subject of the invention is the new compounds of the N-arylmethylene ethylenediaminetriacetate, N-arylmethylene iminodiacetate or N,N'-diarylmethylene ethylenediaminediacetate family and their preparation.

Other subjects of the invention will become apparent on reading the description and examples which follow.

The compounds used in accordance with the invention for protecting against oxidative stress, in particular by scavenging free hydroxyl radicals and complexing iron, are the compounds of formula (I):

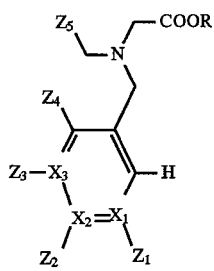

in which:

$Z_1$, $Z_2$ and $Z_3$, independently of one another, represent $NO_2$, COOH, $CF_3$, a halogen atom or an $R_1$, $OR_1$, $SR_1$ or $NR_1R_2$ group, $Z_4$ represents an $R_1$ group;

where R, $R_1$ and $R_2$, independently of one another, represent H or a linear or branched $C_1$ to $C_8$ alkyl group, $X_1$, $X_2$ and $X_3$ represent:

or —N=, provided that if $X_1$=N, then $X_2$=$X_3$=C and there is no $Z_1$ substituent at $X_1$, if $X_2$=N, then $X_1$=$X_3$=C and there is no $Z_2$ substituent at $X_2$, if $X_3$=N, then $X_2$=$X_1$=C and there is no $Z_3$ substituent at $X_3$, that is to say that there is a pyridine ring;

if $X_1$, $X_2$ and $X_3$ all three represent C, there is then a benzene ring;

$Z_5$ represents:

the group: —COOR (a)

or the group:

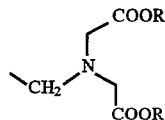

(b)

or the group:

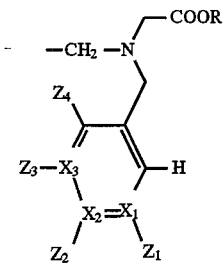

(c)

in which $Z_1$, $Z_2$, $Z_3$, $Z_4$, $X_1$, $X_2$, $X_3$, R, $R_1$ and $R_2$ have the same meanings as above;

and their salts and their metal complexes.

The linear or branched $C_1$-$C_8$ alkyl groups are preferably $C_1$-$C_4$ alkyl groups, such as methyl, ethyl, isopropyl or tert-butyl.

Mention may be made, as salts, of the addition salts with an inorganic acid, such as the acids $H_2SO_4$, HCl, $HNO_3$ or $H_3PO_4$, for example, and the addition salts with an inorganic base, such as NaOH or KOH.

Mention may be made, as metal complexes, of the complexes formed by addition of $ZnCl_2$ or $CaCl_2$, for example.

The new compounds are the compounds of formula (I) in which $Z_1$, $Z_2$, $Z_3$, $Z_4$, $Z_5$, $X_1$, $X_2$, $X_3$, R, $R_1$ and $R_2$ have the meanings indicated above, and their salts and metal complexes, with the exception of the products below, which are already known:

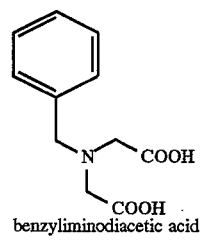
benzyliminodiacetic acid

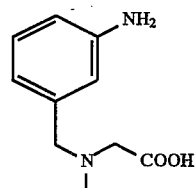
(3-aminobenzyl)iminodiacetic acid

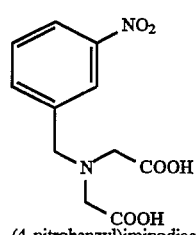
(4-nitrobenzyl)iminodiacetic acid

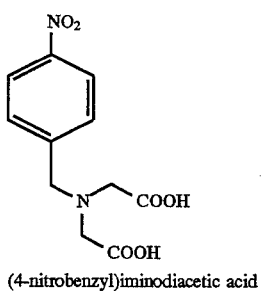
(4-nitrobenzyl)iminodiacetic acid

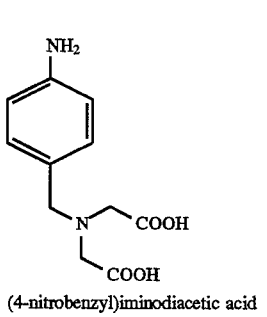
(4-nitrobenzyl)iminodiacetic acid

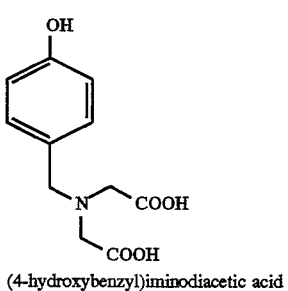
(4-hydroxybenzyl)iminodiacetic acid

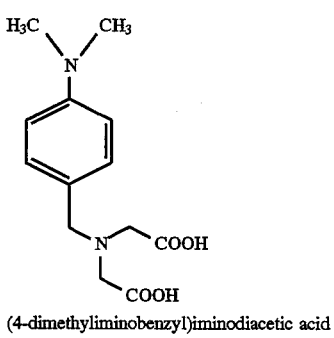
(4-dimethyliminobenzyl)iminodiacetic acid

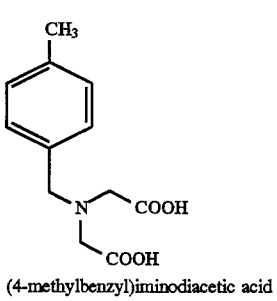
(4-methylbenzyl)iminodiacetic acid

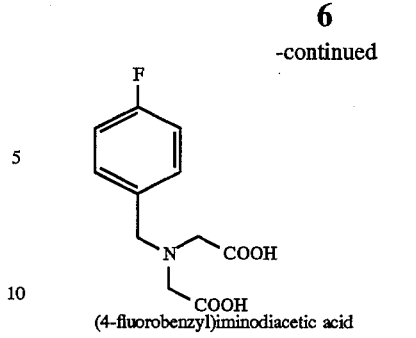
(4-fluorobenzyl)iminodiacetic acid

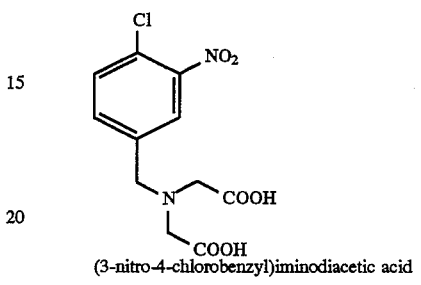
(3-nitro-4-chlorobenzyl)iminodiacetic acid

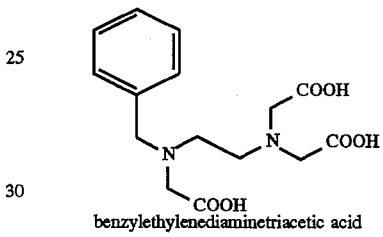
benzylethylenediaminetriacetic acid

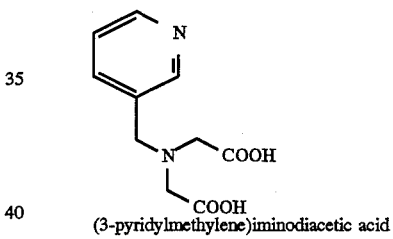
(3-pyridylmethylene)iminodiacetic acid

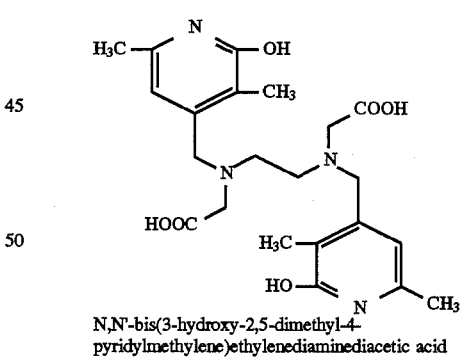
N,N'-bis(3-hydroxy-2,5-dimethyl-4-pyridylmethylene)ethylenediaminediacetic acid and with the proviso that:
when $Z_5$ denotes the group (c) in which $X_1$, $X_2$ and $X_3$ represent C and $Z_4$ denotes H,
at least one of $Z_1$ and $Z_3$ is other than H when $Z_2$ denotes H, Cl, $NO_2$ or $CH_3$ and
$Z_3$ is not H when $Z_1$ denotes OH and $Z_2$ denotes $OCH_3$.

The compounds defined by the formula (I) are used as medicaments, in particular for protecting the body from the harmful effects of free radicals due in particular to oxidative stress. They can particularly be used for treating oxidative stress situations related to pathological conditions in man or in animals, such as cancers, inflammatory conditions, ischemic reperfusion, excess iron, degenerative diseases of the nervous system, or alternatively for treating effects related to exposure to ionizing radiation or to the use of certain medicaments known for generating free radicals, in particular anti-cancer medicaments such as adriamycin, and the like.

The compounds in accordance with the invention can also be used for treating oxidative stress situations related to non-pathological conditions, such as those resulting from exposure to the sun or due to aging. They are used in that case topically for their cosmetic effect on the skin or hair.

The cosmetic and pharmaceutical compositions using the compounds of formula (I) contain a compound of formula (I) or one of its salts or metal complexes in a cosmetically or pharmaceutically acceptable medium.

These compositions contain the compounds of formula (I) in proportions of 0.001 to 10% by weight.

The cosmetic and pharmaceutical compositions can be provided in various forms commonly used in this field and in particular in the form of an ointment, cream, salve, tablet, suspension to be taken orally, injection or gel for pharmaceutical compositions and in the form of a gel, spray, lotion, emulsion or vesicular dispersion for cosmetic compositions.

When the compounds of formula (I) are used in the context of a pharmaceutical treatment, the administration forms can take the oral, topical or parenteral route, the pharmaceutically acceptable vehicle depending on the administration form chosen. The dose is generally between 1 and 100 mg/kg/day.

The cosmetically or pharmaceutically acceptable medium is a medium which is usual in the cosmetic or pharmaceutical field.

The compounds of formula (I) can, according to a preferred embodiment, be used with at least one other active agent (or one other anti-free-radical agent). These agents can be chosen more particularly from:

- antilipoperoxidants, such as vitamin E, trolox or BHT (butylated hydroxytoluene),
- a biological reducing agent such as reduced glutathione and its derivatives or vitamin C and its derivatives,
- a singlet oxygen scavenger, like a carotenoid such as β-carotene,
- a system capable of decomposing hydrogen peroxides, such as enzymes like catalase or peroxidases in the presence of their cosubstrate,
- a system for protecting against the superoxide anion, such as SODs or analogs such as the Mn-desferal complex or copper diisopropylsalicylate,
- a system capable of decomposing organic hydroperoxides, such as glutathione peroxidase or selenium-based systems,
- anti-inflammatory agents,
- UV screening agents,
- penetration promoters,
- and the combinations of these compounds.

The compounds of formula (I) (component (A)) and the active agents or anti-free-radical agents (component (B)) defined above can be used in the same composition or be applied separately, optionally separated in time, using a cosmetic or functional composition containing them.

Moreover, the Applicant company has observed that the compounds (I) according to the invention can be used as antioxidants in order to preserve the compositions containing them.

The present invention also relates to the process for the preparation of the compounds (I) of the invention.

The process varies according to the nature of $Z_5$.

When $Z_5$=—COOR (a), according to process (A), the aldehyde of formula (II) (1 mol):

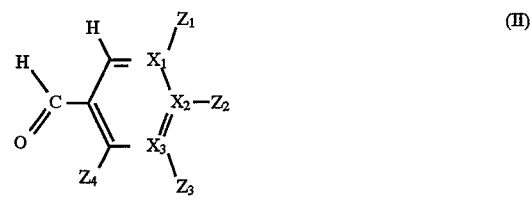

where $X_1$, $X_2$, $X_3$, $Z_1$, $Z_2$, $Z_3$ and $Z_4$ have the meanings already indicated, and the ethyl ester of glycine (1 mol) are brought together in order to obtain the corresponding imine.

When $Z_5$ denotes

according to process (B), the aldehyde of formula (II) (1 mol) and N-acetylethylenediamine (1 mol) are brought together in order to obtain the corresponding imine.

When $Z_5$ denotes

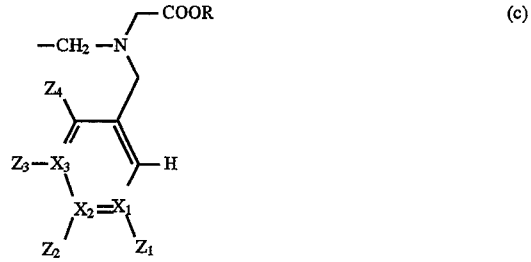

according to process (C), the aldehyde of formula (II) (2 mol) and ethylenediamine (1 mol) are brought together in order to obtain the corresponding diimine.

In each of the three processes, the imine or diimine obtained, which may or may not be isolated, is brought into contact with sodium borohydride or is reduced by catalytic hydrogenation in order to produce the corresponding amine or diamine.

According to process (B), the diamine obtained is then treated with hydrochloric acid in order to hydrolyse the acetyl functional group.

According to process (A), the amine is treated with sodium hydroxide in order to saponify the ethyl ester.

In a subsequent stage, the amine or diamine obtained by processes (A), (B) or (C) is treated in a basic medium, for example in the presence of sodium hydroxide, with bromoacetic acid or one of its esters, in the presence of sodium monohydrogencarbonate. The corresponding product of formula (I) is then recovered. These processes are shown schematically as follows:

GENERAL SYNTHETIC SCHEME

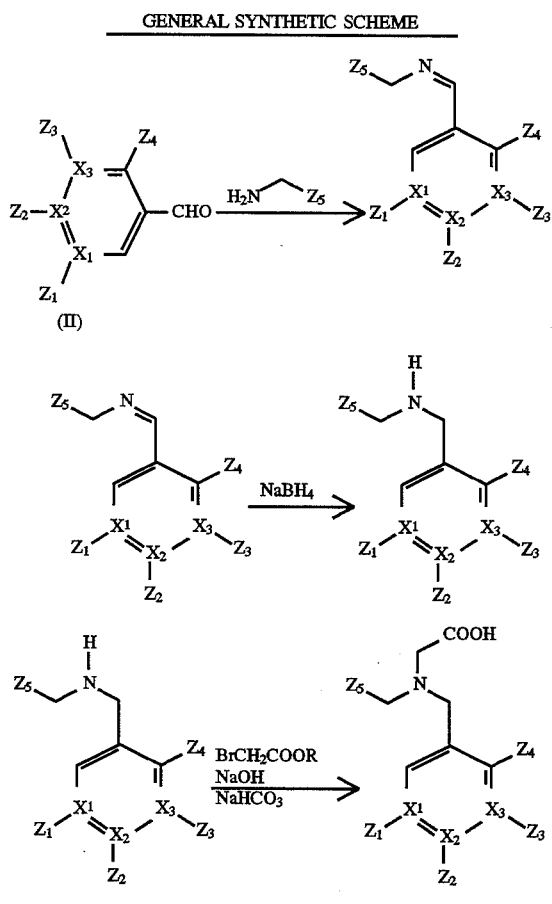

Depending on the nature of $Z_1$, $Z_2$ and $Z_3$, a protection/deprotection stage may be necessary, in particular in the case where one of these substituents is $NH_2$. This additional stage is carried out according to the usual techniques of organic chemistry, as is the final esterification of the compounds according to the formula (I) in which R is H, if free bromoacetic acid is used.

Another subject of the invention is the intermediate diamines resulting from the second stage of the general synthetic process for the compounds (I) illustrated above, in which compounds $Z_5$ represents the group (c), these diamines having the formula:

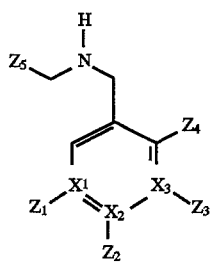

in which $X_1$, $X_2$, $X_3$, $Z_1$, $Z_2$, $Z_3$ and $Z_4$ have the meanings already indicated.

The subject of the invention is more particularly the intermediate compounds of formula:

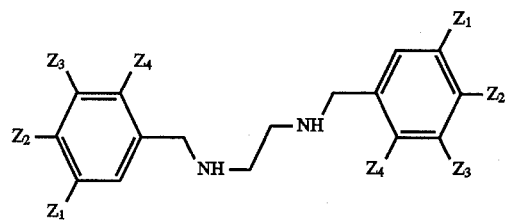

in which $Z_2$ and $Z_4$ represent H and $Z_1$ and $Z_3$ are, independently of one another, $CH_3$, $OCH_3$, $NO_2$ or a halogen atom.

Other characteristics and advantages of the invention will become apparent on reading the examples below.

PREPARATION EXAMPLES

Example 1

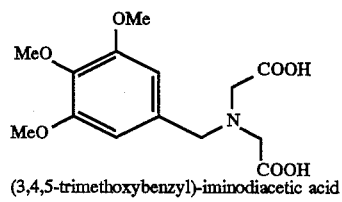

(3,4,5-trimethoxybenzyl)-iminodiacetic acid

Example 2

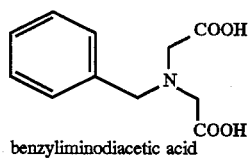

benzyliminodiacetic acid

Example 3

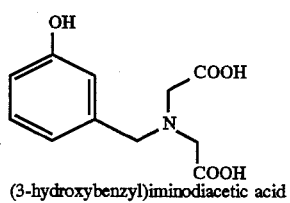

(3-hydroxybenzyl)iminodiacetic acid

Example 4

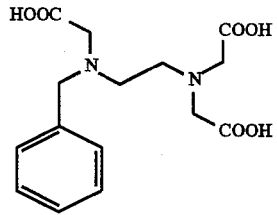

N-benzylethylenediaminetriacetic acid

| Example | Melting point | $^{13}C$ or $^1H$ NMR and MS |
|---|---|---|
| No. 1 | 206–208° C. | consistent |
| No. 2 | 200° C. | consistent |

-continued

| Example | Melting point | $^{13}$C or $^1$H NMR and MS |
|---|---|---|
| No. 3 | 222° C. | consistent |
| No. 4 | 250° C. | consistent |

Examples 5 to 18

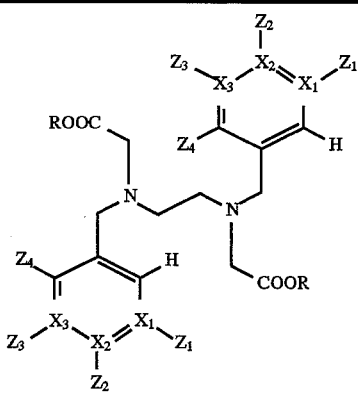

| Example | $X_1$ | $X_2$ | $X_3$ | $Z_1$ | $Z_2$ | $Z_3$ | $Z_4$ | R | M.p. (°C.) | $^{13}$C or $^1$H NMR and MS |
|---|---|---|---|---|---|---|---|---|---|---|
| 5 | C | C | C | H | H | H | Me | H | 198 | consistent |
| 6 | C | C | C | H | H | OH | H | H | 175 | consistent |
| 7 | C | C | C | H | OMe | OH | H | H | >260 | consistent |
| 8 | C | C | C | OMe | OMe | OMe | H | H | 180 | consistent |
| 9 | C | C | C | H | OH | H | H | H | 255 | consistent |
| 10 | C | C | C | H | H | H | H | H | >260 | consistent |
| 11 | C | C | C | OMe | H | H | H | H | 174 | consistent |
| 12 | C | C | C | OMe | H | OMe | H | H | 170 | consistent |
| 13 | C | C | C | OH | NO$_2$ | H | H | H | 220 | consistent |
| 14 | C | C | C | Cl | H | H | H | H | >260 | consistent |
| 15 | C | C | C | H | OMe | Me | Me | H | >260 | consistent |
| 16 | C | C | C | H | H | H | H | isoPr | 50 | consistent |
| 17 | C | C | C | OMe | OMe | OMe | H | Me | 80 | consistent |
| 18 | N | C | C | — | H | H | H | H | 218 | consistent |

GENERAL PROCEDURE

First stage 20 mmol of the starting benzaldehyde of formula (II) are dissolved in 30 ml of methanol. 40 mmol of the amine (20 mmol in the case of ethylenediamine) are added and the mixture is then heated for 30 minutes at 50° C.

The precipitate obtained is filtered off and washed with ethyl ether. A white product is obtained.

Second stage 17 mmol of the imine or diimine are suspended in 100 ml of absolute ethanol. 1 equivalent of sodium borohydride is added portionwise and the mixture is stirred for 1 hour at room temperature.

After evaporation, 20 ml of water are added to the residue and the pH is brought to 8 by addition of hydrochloric acid.

The precipitate is filtered off, washed with water and then dried.

The product is recrystallized from a water/ethanol mixture. A white product is obtained.

In the case of the synthesis of compound No. 9, the product is dissolved in 30 ml of ethanol and then 4 ml of an 8 mol/l solution of hydrochloric acid in ethanol are added. The precipitate obtained is filtered off and then washed with ether. The dihydrochloride of the diamine is obtained in the form of a white product.

Third stage

According to process (C) (Examples No. 5 to 18), 10 mmol of the diamine are dissolved in 15 ml of water containing 10 mmol of sodium hydroxide (30 mmol if the starting material is the dihydrochloride).

20 mmol of bromoacetic acid are dissolved in 25 ml of water at 0° C. containing 20 mmol of sodium monohydrogencarbonate.

The two solutions are mixed and heated at 40° C. for 6 hours, the pH being maintained at approximately 12 by addition of 30% sodium hydroxide solution.

After standing overnight at room temperature, the mixture is acidified with concentrated hydrochloric acid to pH 4–5.

The solution is concentrated under vacuum and the precipitate obtained is filtered off and then recrystallized from a water/ethanol mixture. A white powder is recovered.

According to process (A) (Examples No. 1, 2 and 3), 10 mmol of amine in 20 ml of water are stirred beforehand for 30 minutes at room temperature in the presence of 10 mmol of NaOH. The crude mixture obtained is then treated with 10 mmol of bromoacetic acid dissolved in 25 ml of water containing 10 mmol of $NaHCO_3$, as indicated above for process (C).

According to process (B) (Example No. 4), 10 mmol of amine in 20 ml of 4N HCl are brought to reflux for 24 hours. The crude mixture obtained is then brought back to basic pH and treated with 30 mmol of bromoacetic acid dissolved in 30 ml of water containing 30 mmol of $NaHCO_3$ in order to obtain the corresponding N-benzylethylenediamine derivative, as indicated above for process (C).

COSMETIC FORMULATION EXAMPLES

EXAMPLE A

The following emulsion is prepared according to conventional techniques by using the constituents below.

| | |
|---|---|
| Compound of Example 1 | 0.1 g |
| Polyethyleneglycol oxyethylenated with 50 mol of ethylene oxide | 3 g |
| Monodiglycerylstearate | 3 g |
| Liquid paraffin | 24 g |
| Cetyl alcohol | 5 g |
| Water | q.s. for 100 g |

A white emulsion is obtained, intended to be applied topically to the skin region to be protected.

EXAMPLE B

The following emulsion is prepared according to conventional techniques by using the constituents below.

| | |
|---|---|
| Compound of Example 2 | 0.02 g |
| Octylpalmitate | 10 g |
| Glycerylisostearate | 4 g |
| Liquid paraffin | 24 g |
| Vitamin E | 1 g |
| Glycerol | 3 g |
| Water | q.s. for 100 g |

A white emulsion is obtained, intended to be applied topically to the skin region to be protected.

EXAMPLE C

The following formulation is prepared according to conventional techniques by using the constituents below.

| | |
|---|---|
| Compound of Example 2 | 0.02 g |
| Jojoba oil | 13 g |
| Methyl and isopropyl para-hydroxybenzoates | 0.05 g |
| Potassium sorbate | 0.3 g |
| Cyclopentadimethylsiloxane | 10 g |
| Stearyl alcohol | 1 g |
| Stearic acid | 4 g |
| Polyethyleneglycol stearate | 3 g |
| Vitamin E | 1 g |
| Glycerol | 3 g |
| Water | q.s. for 100 g |

A white emulsion is obtained, intended to be applied topically to the skin region to be protected.

EXAMPLE D

The following emulsion is prepared according to conventional techniques by using the constituents below.

| | |
|---|---|
| Compound of Example 6 | 0.01 g |
| Polyethyleneglycol oxyethylenated with 50 mol of ethylene oxide | 3 g |
| Monodiglycerylstearate | 3 g |
| Liquid paraffin | 24 g |
| Cetyl alcohol | 5 g |
| Water | q.s. for 100 g |

A white emulsion is obtained, intended to be applied topically to the skin region to be protected.

EXAMPLE E

The following emulsion is prepared according to conventional techniques by using the constituents below.

| | |
|---|---|
| Compound of Example 7 | 0.02 g |
| Octylpalmitate | 10 g |
| Glycerylisostearate | 4 g |
| Liquid paraffin | 24 g |
| Vitamin E | 1 g |
| Glycerol | 3 g |
| Water | q.s. for 100 g |

A white emulsion is obtained, intended to be applied topically to the skin region to be protected.

EXAMPLE F

The following formulation is prepared according to conventional techniques by using the constituents below.

| | |
|---|---|
| Compound of Example 6 | 0.02 g |
| Jojoba oil | 13 g |
| Methyl and isopropyl para-hydroxybenzoates | 0.05 g |
| Potassium sorbate | 0.3 g |
| Cyclopentadimethylsiloxane | 10 g |
| Stearyl alcohol | 1 g |
| Stearic acid | 4 g |
| Polyethyleneglycol stearate | 3 g |
| Vitamin E | 1 g |
| Glycerol | 3 g |
| Water | q.s. for 100 g |

A white emulsion is obtained, intended to be applied topically to the skin region to be protected.

PHARMACEUTICAL FORMULATION EXAMPLES

G—ORAL ROUTE

1) Tablet

| | |
|---|---|
| Compound of Example 2 | 0.001 g |
| Starch | 0.114 g |
| Dicalcium phosphate | 0.020 g |
| Lactose | 0.060 g |
| Magnesium stearate | 0.005 g |

After compacting, a 0.2 g tablet is obtained.

2) Suspension to be taken orally

| | |
|---|---|
| Compound of Example 2 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavor q.s. | |
| Purified water | q.s. for 5 ml |

3) Tablet

| | |
|---|---|
| Compound of Example 6 | 0.001 g |
| Starch | 0.114 g |
| Dicalcium phosphate | 0.020 g |
| Lactose | 0.060 g |
| Magnesium stearate | 0.005 g |

After compacting, a 0.2 g tablet is obtained.

4) Suspension to be taken orally

| | |
|---|---|
| Compound of Example 8 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavor q.s. | |
| Purified water | q.s. for 5 ml |

H—ADMINISTRATION BY INJECTION

3 ml injectable phial

| | |
|---|---|
| Compound of Example 2 | 0.002 g |
| Sodium hydroxide | 0.0007 g |
| Water for injectable preparation | q.s. for 3 ml |

3 ml injectable phial

| | |
|---|---|
| Compound of Example 9 | 0.002 g |
| Sodium hydroxide | 0.0007 g |
| Water for injectable preparation | q.s. for 3 ml |

We claim:

1. Compound of formula (I):

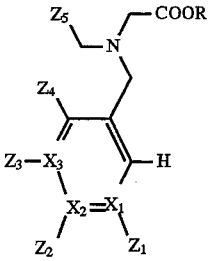 (I)

in which $Z_1$, $Z_2$ and $Z_3$, independently of one another, represent $NO_2$, COOH, $CF_3$, a halogen atom or an $R_1$, $OR_1$, $SR_1$ or $NR_1R_2$ group, $Z_4$ represents an $R_1$ group;

where R, $R_1$ and $R_2$, independently of one another, represent H or a linear or branched $C_1$ to $C_8$ alkyl group, $X_1$, $X_2$ and $X_3$ represent:

$Z_5$ represents:

the group:

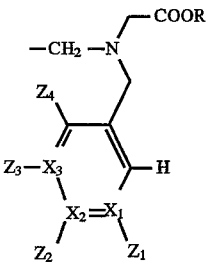 (c)

in which $Z_1$, $Z_2$, $Z_3$, $Z_4$, $X_1$, $X_2$, $X_3$, R, $R_1$ and $R_2$ have the same meanings as above; with the proviso that, when $Z_5$ denotes the group (c) in which $Z_4$ denotes H, at least one of $Z_1$ and $Z_3$ is other than H when $Z_2$ denotes H, Cl, $NO_2$ or $CH_3$ and $Z_3$ is not H when $Z_1$ denotes OH and $Z_2$ denotes $OCH_3$; or its salts or metal complexes.

2. Compound of formula (I) according to claim 1, selected from the group consisting of N,N'-di(2-methylbenzyl)ethylenediaminediacetic acid, N,N'-di(3-hydroxybenzyl) ethylenediaminediacetic acid, N,N'-di(3,4,5-trimethoxybenzyl)ethylenediaminediacetic acid and its methyl ester, N,N'-di(4-hydroxybenzyl) ethylenediaminediacetic acid, N,N'-di(3-methoxybenzyl) ethylenediaminediacetic acid, N,N'-di(3,5-dimethoxybenzyl)ethylenediaminediacetic acid, N,N'-di(3-hydroxy-4-nitrobenzyl)ethylenediaminediacetic acid, N,N'-di(3-chlorobenzyl)ethylenediaminediacetic acid, N,N'-di(2,3-dimethyl-4-methoxybenzyl) ethylenediaminediacetic acid, and their salts and metal complexes.

* * * * *